(12) United States Patent
Igumnov et al.

(10) Patent No.: US 6,664,431 B2
(45) Date of Patent: Dec. 16, 2003

(54) PROCESS FOR PRODUCING FLUORINATED ALIPHATIC COMPOUNDS

(75) Inventors: Sergei Mikhailovich Igumnov, Moscow (RU); Galina Ivanovna Lekontseva, Perm (RU)

(73) Assignee: Zakrytoe Aktsionernoe Obschestvo Nauchno-Proizvodstvennoe Obiedinenie "Pim-Invest", Moscow (RU)

( * ) Notice: Subject to any disclaimer, the term of this patent is extended or adjusted under 35 U.S.C. 154(b) by 0 days.

(21) Appl. No.: 09/808,410

(22) Filed: Mar. 14, 2001

(65) Prior Publication Data

US 2002/0177742 A1 Nov. 28, 2002

(51) Int. Cl.$^7$ .................. C07C 17/60; C07C 17/62; C07C 17/64; C07C 21/18; C07C 21/20; C07C 21/22

(52) U.S. Cl. ............... 570/135; 570/153; 526/406; 526/915

(58) Field of Search ............... 570/142, 166, 570/123, 153, 124, 134, 135

(56) References Cited

U.S. PATENT DOCUMENTS

| | | | |
|---|---|---|---|
| 3,020,321 A | | 2/1962 | Gibbs |
| 3,555,100 A | | 1/1971 | Garth et al. |
| 3,862,212 A | * | 1/1975 | Nomori et al. |
| 4,358,412 A | | 11/1982 | Ezzell et al. |
| 4,594,458 A | | 6/1986 | Krespan |
| 5,045,634 A | * | 9/1991 | Fernandez et al. ........... 570/170 |
| 5,347,058 A | * | 9/1994 | Farnham ..................... 570/170 |

FOREIGN PATENT DOCUMENTS

SU  659555  5/1977

OTHER PUBLICATIONS

English claim of SU 659555 of May 1977.
Blake, P.G., et al., "The Thermal Decomposition of Fluorinated Esters," *International Journal of* Chemical Kinetics, vol 14, pp 291–297, 1982.
*2–Hydropentafluoropropylene. Preparation, Properties And Use*, Ministry of Chemical Industry, Moscow, 1979, pp 3–6 in English and pp 1–2 in Russian.
Zapevalova, T. B., et al., "Synthesis and Reactions of Oxygen–Containing Fluorooganic Compounds," *zhurnal Organicheskoi Khimii*, vol. XIV, 1978, p487 in English, pp487–490 RU.
Aktaev, N. P., et al., "Comparison of the Electron Effects of Nitrile and Trifluoromethyl Groupings," *Izvestiya Akademii Nauk SSSR*, 1977, p1112 in English, pp1 + 1112–7 Russian.

* cited by examiner

*Primary Examiner*—Johann Richter
*Assistant Examiner*—Karl J. Puttlitz
(74) *Attorney, Agent, or Firm*—Ladas & Parry

(57) ABSTRACT

The present invention relates to a process for producing fluorinated aliphatic compounds by pyrolysis of perfluorocarboxylic acids and their derivatives—halides and esters. The pyrolysis is carried out in the presence of a catalyst consisting of a carrier most preferably selected from the series comprising active carbon, magnesium oxide, calcium oxide, barium oxide, zinc oxide, aluminum oxide, nickel oxide, oxides of silicon promoted with alkali metal halides, selected from the series comprising fluorides, chlorides bromides, iodides of sodium, potassium, rubidium, cesium, at a temperature in the range of from about 100° C. to about 450° C.; with producing fluorinated aliphatic compounds selected from the series comprising perfluoroolefins, polyfluoroolefins and their derivatives; and also in the presence additionally of hydrogen fluoride with the formation of fluorinated aliphatic compounds selected from the series comprising polyfluoroalkanes and their derivatives.

24 Claims, No Drawings

PROCESS FOR PRODUCING FLUORINATED ALIPHATIC COMPOUNDS

FIELD OF THE ART

The present invention relates to the fluoroorganic chemistry, particularly to a process for producing fluorinated aliphatic compounds by pyrolysis of perfluoro- and polyfluorocarboxylic acids and their derivatives—halides and esters. The products of the pyrolysis, depending on the conditions under which it is carried out, are fluorinated olefins, perfluoroalkylvinyl ethers and polyfluoroalkanes. Fluorinated olefins and perfluoroalkylvinyl ethers are used as starting materials for obtaining polymer materials with improved operational characteristics, lubricating oils, elastomers, ion-exchange membranes for the electrolysis of aqueous solutions of alkali metal halides, etc. Polyfluoroalkanes, owing to their chemical inertness and thermal stability, find application as components of mix coolants, actuating fluids of thermocompressors, porophores in manufacturing foamed plastics and polyurethane foams, gas dielectrics, propellants, inert solvents, reagents for dry etching in manufacturing integrated circuits, and also in formulations of fire-extinguishing means.

At present a necessity is felt in the provision of an industrial process for producing fluorinated olefins, polyfluoroalkanes, perfluoroalkylvinyl ethers from different available organofluorine compounds under relatively mild reaction conditions with a high yield.

PRIOR ART

It is known that polyfluoroalkanes, particularly such as promising ozone-safe Freons 125, 227ea, are produced mainly by the hydrofluorination of perfluoroolefins—tetrafluoroethylene (TFE) and hexafluoropropylene (HFP), the production of which involves definite difficulties. TFE is explosion-hazardous, highly toxic, and self-polymerizes. TFE and HFP are produced by the high-temperature pyrolysis of chlorine- and fluorine-containing hydrocarbons, whose production in accordance with the decision of the Montreal Protocol concerning substances destroying the ozone layer is reduced because they deteriorate considerably the ecological situation. Therefore the possibility of obtaining polyfluoroalkanes (Freon 125, 227ea and the like) and olefins as such (TFE, HFP) from other available starting materials, namely, perfluoro- and polyfluorocarboxylic acids and their derivatives by a more simple process is a very urgent problem. The claimed process solves this problem.

It is known that in the pyrolysis of esters of perfluoroalkoxycarboxylic acids of the formula $$ICF_2CF_2OQCF(CF_3)COOR,$$

where

Q is $OCF_2CF(CF_3)[OCF(CF_3)CF_2]_m$, $[OCF(CF_3)CF_2]_n$;

m is 0 to 7;

n is 1 to 4;

R is ($C_1$–$C_6$) alkyl vinyl ethers are formed above a layer of carbonate, phosphate, sulfite, sulfate of an alkali or alkali-earth metal (U.S. Pat. No. 4,594,458, C07C 43/16, publ. 10.06.86). In this process, from an ester first a salt is obtained by treating $NaHCO_3$ in a methanol solution, and then the salt is subjected to pyrolysis at 140–260° C. In accordance with this process, perfluoro (8-iodo-4-methyl-3,6-dioxaoctene-1) is obtained with a yield of 71.8%.

A disadvantage of this process is the necessity of carrying out the intermediate step of obtaining an alkali metal salt and the necessity of drying this salt thoroughly, because the presence of moisture leads to the formation of by-products. Furthermore, toxic, fire- and explosion-hazardous methanol is used for carrying out the reaction.

In the pyrolysis of ethyl esters of pentafluoropropionic and heptafluorobutyric acid at 350–413° C. and a pressure of about 8–80 gPa tetrafluoroethylene and hexafluoropropylene are formed, respectively, with a yield of about 30%, as well as an insignificant amount of pentafluorethane and heptafluoropropane (Int. J. Chem. Kinet., 1982, 14, No. 3, 291).

Known in the art is pyrolysis of polyfluoroalkoxyperfluoropropionic acid fluorides on sodium carbonate at 200–220° C., which gives polyfluoroalkylperfluorovinyl ethers with a yield of 85–91% (Zhurnal Organicheskoi Khimii, 1978, 14, No. 3, 487). The pyrolysis proceeds in accordance with the following scheme:

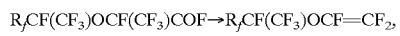

$$R_fCF(CF_3)OCF(CF_3)COF \rightarrow R_fCF(CF_3)OCF=CF_2,$$

where $R_f$ is $CF_3CF_2$, $CF_3(CF_2)_3$, $ClCF_2CF_2$.

$Na_2CO_3$ is a reagent which is consumed in the process of the synthesis, forming NaF.

In the pyrolysis of polyfluorocarboxylic acid halides of the formula $XC_nF_{2n}COI$ (wherein X is H, F; n>1; I is a haloid) at 200–500° C., fluoroolefins of the formula $XC_nF_{2n-1}$ are formed (U.S. Pat. No. 3,020,321, 260-653.3, publ. 06.02.62). The reaction is carried out with oxides of Group IIA metals and silicon or with oxygen-containing salts of Group IA and Group IIA metals of the Periodic System.

The disadvantages of this process are a high reaction temperature (mainly 380° C.) and direct participation of oxides and oxygen-containing salts in the process with the formation of inorganic fluorides, which makes the process unstable.

Decarbonylation of polyfluorocarboxylic acid fluorides is known in the art, which leads to obtaining polyfluoroalkanes in accordance with the following scheme:

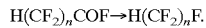

$$H(CF_2)_nCOF \rightarrow H(CF_2)_nF.$$

The reaction proceeds in the presence of a catalyst: anhydrous aluminum oxide (RU 659555, C07C 19/08, publ. 30.04.79) or under heating acyl fluoride with antimony pentafluoride (U.S. Pat. No. 3,555,100, C07C 19/08, publ. 12.01.71). As a result, 1-hydroperfluorohexane was obtained with a yield of 87–93%.

The prior-art processes cited above depend on starting materias, because monohydroperfluoroalkanes can be produced only from corresponding monohydroperfluorocarboxylic acid fluorides, which are not always available. They do not allow selective introduction of hydrogen into the carbon chain either.

High-temperature decarboxylation (620° C. and 120 mm Hg) of 2-hydroperfluorobutyric acid gives 2-hydropentafluoropropylene with the yield of 92% (2-Hydropentafluoro propylene. Khim. Promyshl. Ser. Prikladnaya Khimiya, Moscow, NIITEK-hiM, 1979, pp. 1–2). The reaction proceeds in accordance with the following scheme:

$$CF_3CHFCF_2COOH \rightarrow CF_3CH=CF_2.$$

Decarboxylation of α-hydrohexafluoroisobutyric acid in dimethyl formamide gives 2,2-dihydrohexafluoropropane with the yield of 65% (Izv. AN SSSR, Ser. Khimiya, 1977, No. 5, 1112).

The reaction proceeds in accordance with the following scheme:

$$(CF_3)_2CHCOOH \rightarrow CF_3CH_2CF_3.$$

With the help of this process only dihydroperfluoroalkanes can be produced.

It is known that decarboxylation of fluorocarboxylic acids of the formula $R(CFR^1)_n(CFR^2)_mOCF(CF_2X)COOH$, where R is $SO_2Z$, $POZ_2$, COZ; Z is $OR^3$, F, Cl, Br, I; $R^3$ is alkyl or aryl; $R^1$ and $R^2$ each are F, Cl, perfluoro- or chlorofluoroalkyl; X is Cl, Br, I; n is from 0 to 3; m is from 0 to 3, in the presence of an activator $Na_2CO_3$, ZnO or $SiO_2$ in an organic solvent (mono-, di- or tetraglyme) at 50–150° C. makes it possible to obtain corresponding vinyl ethers of the following formula: $R(CFR^1)_n(CFR^2)_mOCF=CF_2$ (U.S. Pat. No. 4,358,412, C07F 9/113, publ. 09.11.82).

DISCLOSURE OF THE INVENTION

It is an object of the present invention to provide a universal industrial process for producing fluorinated aliphatic compounds with a high yield from available starting materials.

Another object of the present invention is to provide a process for producing fluorinated aliphatic compounds that are fluorinated olefins and perfluoroalkylvinyl ethers, by pyrolysis of perfluoro- and polyfluorocarboxylic acids, their halides and esters.

Still another object of the present invention is to provide a process for producing fluorinated aliphatic compounds that are polyfluoroalkanes, by pyrolysis of perfluoro- and polyfluorocarboxylic acids, their halides and esters in the presence of hydrogen fluoride.

Said objects are accomplished by the present invention, wherein a process for producing fluorinated aliphatic compounds is disclosed, consisting in carrying out pyrolysis of perfluoro- and polyfluorocarboxylic acids and their derivatives selected from the acid halides and esters, on a catalyst consisting of a carrier, most preferably selected from the series comprising active carbon, magnesium oxide, calcium oxide, barium oxide, zinc oxide, aluminum oxide, nickel oxide, oxides of silicon promoted with alkali metal halides at a temperature of 100–450° C., optionally in the presence of hydrogen fluoride.

Carrying out pyrolysis in the absence of hydrogen fluoride leads to the formation of fluorinated olefins and perfluoroalkylvinyl ethers. In the case of pyrolysis carried out in the presence of hydrogen fluoride polyfluoroalkanes are obtained as the target end products.

BEST VARIANTS OF CARRYING OUT THE INVENTION

The process of pyrolysis is carried out continuously in a flow-through system, for which purpose a tubular reactor is used. The reactor is provided with electric heating, with a thermocouple sheath, with pipes for feeding the starting components and discharging the reaction products. The factor of filling the reactor with a catalyst is up to 0.8. The catalyst consists of a carrier preferably selected from the series comprising active carbon, silicon oxides, oxides of metals of Groups II, III, IV of the Periodic System, oxides of transition metals promoted with alkali metal halides. Compounds selected from the series comprising fluorides, chlorides, bromides, iodides of sodium, potassium, rubidium, cesium are used as said metal halides. It is most preferable to use magnesium oxide, calcium oxide, barium oxide, zinc oxide, aluminum oxide, nickel oxide as the above-indicated metal oxides. Examples of such catalysts can be $KF/SiO_2$, $NaF/SiO_2$, $CsF/NiO$, $NaF/Al_2O_3$, $KF/CaO$, $CsF/SiO_2$, $NaCl/C_{act.}$, $KF/MgO$, $KI/Al_2O_3$, etc. Active carbon and silicon dioxide, promoted with potassium fluoride, are the most preferable catalysts.

Optimal content of halides in the catalyst is from 20 to 50 wt. %. A reduction of the halide concentration to less than 20 wt. % leads to reducing the yield of the target product. An increase of the halide concentration above 50 wt. % does not influence substantially the process and is, therefore, inexpedient.

For preparing the catalyst, the carrier is mixed with an aqueous solution of an alkali metal halide, kept for up to 24 hours at room temperature, and then dried in a drying cabinet at 180–210° C. to constant weight.

For creating a reaction zone, the prepared catalyst is charged into the reactor and heated in a stream of dry nitrogen, with the temperature increased gradually from 180 to 350° C. for four hours. Then the starting reagent is fed into said reaction zone, said starting reagent being selected from the series comprising perfluorocarboxylic acids, polyfluorocarboxylic acids of a normal or isostructure, optionally containing a haloid other than fluorine, or their derivatives, such as acid halides or esters. Examples of said starting reagent can be perfluoropropionic acid, perfluorobutyric acid, perfluorovaleric acid, perfluoropelargonic acid, ω-hydroperfluorobutyric acid, ω-hydroperfluorovaleric acid, perfluoroisobutyric acid, perfluoropropionic acid chloride, perfluoropropionic acid fluoride, perfluoropropionic acid bromide, perfluoroisobutyric acid fluoride, perfluorobutyric acid chloride, perfluorovaleric acid fluoride, perfluorovaleric acid chloride, perfluoroenanthic acid chloride, perfluoropelargonic acid fluoride, ω-hydroperfluorovaleric acid fluoride, ω-hydroperfluoropropionic acid fluoride, perfluoropropoxyisopropionic acid fluoride, perfluoropropoxyisopropionic acid chloride, perfluoromethoxyisopropionic acid fluoride, 2-bromoperfluoroethoxyisopropionic acid fluoride, methyl ester of perfluoropropionic acid, ethyl ester of perfluoropropionic acid, methyl ester of perfluoroisobutyric acid, ethyl ester of perfluorovaleric acid, ethyl ester of perfluoroenanthic acid, methyl ester of perfluoropelargonic acid, methyl ester of ω-hydroperfluorovaleric acid, ethyl ester of perfluoropropoxyisopropionic acid, methyl ester of perfluoropropoxyisopropionic acid, methyl ester of 2-bromoperfluoroethoxyisopropionic acid, methyl ester of perfluoropentoxyisopropionic acid.

The process of pyrolysis of the starting reagent in the presence of a catalyst is carried out in a sufficiently wide temperature range of 100 to 450° C. At a temperature below 100° C. the reaction slows down to such an extent that the conversion of the starting compounds does not exceed 5–10%. A temperature increase to 450° C. causes destruction of the starting components and of the target products. For obtaining fluorinated olefins and perfluoroalkylvinyl ethers the temperature of 170–250° C. is preferable. The synthesis of polyfluoroalkanes should be carried out preferably at a temperature of 250–350° C.

The above-described catalytic pyrolysis of perfluorocarboxylic acids, polyfluorocarboxylic acids and their derivatives gives fluorinated olefins and perfluoroalkylvinyl ethers, such as, e.g., tetrafluoroethylene, hexafluoropropylene, perfluoro-1-butene, perfluoro-2-butene, perfluoro-2-pentene, perfluoro-2-hexene, perfluoro-2-octene, perfluoro-3-octene, perfluoro-4-octene, 1-hydroperfluoro-2-butene, trifluoroethylene, perfluoropropylvinyl ether, perfluoromethylvinyl ether, perfluoropentylvinyl ether, 2-bromoperfluoroethylvinyl ether.

In the case the above-described catalytic pyrolysis of perfluorocarboxylic acids, polyfluorocarboxylic acids and their derivatives is carried out with introducing hydrogen fluoride into the reaction zone, there takes place hydrofluorination of the fluorinated olefins and perfluoroalkylvinyl ethers which form as a result of the pyrolysis, and the obtained final products are polyfluoroalkanes containing at least one hydrogen atom, and ethers, for instance, 1-hydropentafluoroethane, 2-hydroheptafluoropropane, 2-hydroperfluorobutane, 1,3-dihydroperfluorobutane, 2-hydroperfluoroethylpropyl ether, 1-bromo-4-hydroperfluorodiethyl ether.

When producing polyfluoroalkanes, a 1.5–2.0-fold molar excess of hydrogen fluoride to the starting reagent is optimal. Feeding a smaller amount of hydrogen fluoride leads to an appreciable lowering of the yield of the target products, whereas an increase in the amount of the fed hydrogen fluoride is inexpedient.

Hydrogen fluoride can be introduced into the reaction zone simultaneously with the starting reagent or after performing the pyrolysis step. In this case hydrogen fluoride is fed to the reaction zone through the pipe into the middle part of the reactor.

The products of pyrolysis, i.e., fluorinated olefins and perfluoroalkylvinyl ethers, are condensed in a cooled collecting tank.

When producing polyfluoroalkanes, there remains unreacted hydrogen fluoride. To remove it, acid products of the pyrolysis are first washed with an alkali solution, then neutralized additionally on a column with a lime chemical absorber, and after that condensed at a temperature of –30 to –50° C. The target products are isolated from the condensate by rectification and then identified by IR and NMR spectroscopy techniques.

In accordance with the present process there have been produced, in particular, 1-hydropentafluoroethane (Freon 125), 2-hydroheptafluoropropane (Freon 227ea) with the yield of 98%, and other polyfluoroalkanes, whose yield was not lower than 85%. In accordance with the present process there have been also produced various perfluoroolefins, polyfluoroolefins and perfluoroalkylvinyl ethers with a yield of up to 95%.

EXAMPLES

The Examples which follow are presented for illustrating the invention but for limiting it.

Example 1
Synthesis of Perfluoro-2-butene

A 0.3 dm³-capacity tubular reactor made from stainless steel, provided with electric heating, with a thermocouple sheath, with pipes for feeding the starting components and discharging the reaction products, is charged with about 0.23 dm³ of a catalyst which is silicon dioxide promoted with potassium fluoride in an amount of 35 wt. %. The catalyst is heated in a stream of dry nitrogen with a gradual temperature increase from 180 to 350° C. for four hours. Then the temperature is lowered to 240° C., and 40 g of methyl ester of perfluorovaleric acid are fed with the rate of 20 g/hour. The gas mixture outgoing from the reactor is condensed in a trap cooled down to –30° C., and subjected to low-temperature rectification, as a result of which 27.4 g of perfluoro-2-butene are obtained. The yield of the target product is 95.1%.

Example 2

Synthesis of 2-Hydroheptafluoropropane

A tubular reactor described in Example 1 is charged with 0.23 dm³ of a catalyst which is active carbon promoted with potassium fluoride in an amount of 30 wt. %. The catalyst is heated in a stream of dry nitrogen with a gradual temperature increase from 180 to 350° C. for four hours. Then the temperature is lowered to 250° C., and 50 g of methyl ester of perfluoroisobutyric acid and 7.5 g of hydrogen fluoride are fed during 1 hour.

The gas mixture outgoing from the reactor is passed through a solution of potassium, hydroxide, collected in a trap cooled down to –30° C., and subjected to low-temperature rectification. 36.5 g of the target product are obtained, this corresponding to the yield of 98.0%.

Example 3

Synthesis of 1-Hydropentafluoroethane

A tubular reactor described in Example 1 is charged with about 0.21 dm³ of a catalyst which is silicon dioxide promoted with cession fluoride in an amount of 40 wt. %. The catalyst is heated in a stream of dry nitrogen with a gradual temperature increase from 180 to 350° C. for four hours. Then the temperature is lowered to 260° C., and 20 g of perfluoropropionic acid fluoride and 4 g of hydrogen fluoride are fed during 1 hour, the hydrogen fluoride being fed into the middle part of the reactor.

The gas mixture outgoing from the reactor is condensed in a trap cooled down to –30° C., and subjected to low-temperature rectification. 13 g of the target product indicated in the heading of this Example are obtained, this corresponding to the yield of 89.7%.

The subsequent syntheses (Examples 4–19) are carried out similarly to Examples 1, 2. The synthesis conditions and results are presented in the Table.

Thus, a unique process has been developed for the synthesis of fluorinated aliphatic compounds by a catalytic pyrolysis of different starting reagents: perfluorocarboxylic acids, polyfluorocarboxylic acids and their derivatives. The present process makes it possible to produce perfluoroolefins, polyfluoroolefins and perfluoroalkylvinyl ethers with a yield of up to 95%, as well as to produce polyfluoroalkanes with a yield of up to 98% with a selective introduction of hydrogen into the carbon chain.

TABLE

Pyrolysis conditions and resutls

| Nos. | Starting compound | | Catalyst Composition | Content of promotor, wt. % | Temp., ° C. |
|---|---|---|---|---|---|
| 4 | Methyl ester of perfluoroisobutyric acid | $CF_3-CF(CF_3)-COOCH_3$ | $KF/SiO_2$ | 30 | 300 |
| 5 | Perfluorovaleric acid | $CF_3(CF_2)_3COOH$ | $KF/SiO_2$ | 30 | 270 |
| 6 | Perfluoropropoxyisopropionic acid fluoride | $CF_3CF_2CF_2OCF(CF_3)COF$ | $CsF/NiO$ | 20 | 170 |
| 7 | Ethyl ester of perfluoropropoxyisopropionic acid | $CF_3CF_2CF_2OCF(CF_3)COOC_2H_5$ | $NaF/Al_2O_3$ | 30 | 300 |
| 8 | 2-Bromoperfluoroethoxyisopropionic acid fluoride | $BrCF_2CF_2OCF(CF_3)COF$ | $KF/CaO$ | 20 | 200 |
| 9 | Ethyl ester of perfluoropropionic acid | $CF_3CF_2COOC_2H_5$ | $CsF/SiO_2$ | 40 | 280 |
| 10 | Perfluoroisobutyric asid fluoride | $CF_3-CF(CF_3)-COF$ | $NaCl/C_{akt.}$ | 35 | 300 |
| 11 | ω-Hydroperfluorovaleric acid | $H(CF_2)_4COOH$ | $KF/MgO$ | 25 | 130 |
| 12 | Perfluorovaleric acid | $CF_3(CF_2)_3COOH$ | $KI/Al_2O_3$ | 30 | 160 |
| 13 | Perfluoropropionic acid fluoride | $CF_3CF_2COF$ | $KF/C_{act.}$ | 30 | 260 |
| 14 | Perfluoropropionic acid chloride | $CF_3CF_2COCl$ | $KF/C_{act.}$ | 20 | 290 |
| 15 | ω-Hydroperfluoropropyonic acid fluoride | $HCF_2CF_2COF$ | $KF/C_{act.}$ | 30 | 200 |
| 16 | Methyl ester of perfluoromethoxyisopropyonic acid | $CF_3OCF(CF_3)COOCH_3$ | $KF/SiO_2$ | 25 | 220 |
| 17 | Methyl ester of perfluoropropionic acid | $CF_3CF_2COOCH_3$ | $KF/C_{act.}$ | 30 | 270 |
| 18 | Methyl ester of perfluoroisobutyric acid | $CF_3-CF(CF_3)-COOHCH_3$ | $NaF/C_{act.}$ | 50 | 300 |
| 19 | Methyl ester of perfluorovaleric acid | $CF_3CF_2CF_2COOCH_3$ | $KF/SiO_2$ | 20 | 250 |

| Nos. | Metering rate, g/h Starting Comp-d | HF | Duration, h | Resulting compound | | Amount of product, g | Yield, % |
|---|---|---|---|---|---|---|---|
| 4 | 10 | | 3.0 | Hexafluoropropylene | $CF_3CF=CF_2$ | 18.0 | 91.8 |
| 5 | 20 | | 2.0 | Perfluoro-1,2-butenes | $CF_3CF=CFCF_3$ $CF_3CF_2CF=CF_2$ | 27.6 | 91.1 |
| 6 | 16 | | 2.0 | Perfluoropropylvinyl ether | $CF_3CF_2CF_2OCF=CF_2$ | 23.0 | 89.8 |
| 7 | 14 | | 2.0 | Perfluoropropylvinil ether | $CF_3CF_2CF_2OCF=CF_2$ | 13.2 | 60.6 |
| 8 | 20 | | 1.0 | Perfluoro-2-bromoethylvinyl | $BrCF_2CF_2OCF=CF_2$ | 15.4 | 95.1 |

TABLE-continued

| | | | | | | | |
|---|---|---|---|---|---|---|---|
| | | | | ether | | | |
| 9 | 20 | 4.0 | 1.5 | 1-Hydropentafluoroethane | $CF_3CF_2H$ | 17.6 | 94.2 |
| 10 | 15 | 2.5 | 2.0 | 2-Hydropentafluoropropane | $CF_3CFHCF_3$ | 21.4 | 90.5 |
| 11 | 20 | 3.0 | 2.0 | 1,3-Dihydroperfluorobutane | $HCF_2CF_2CFHCF_3$ | 28.0 | 85.3 |
| 12 | 20 | 2.7 | 1.5 | 2-Hydroperfluorobutane | $CF_3CF_2CFHCF_3$ | 21.2 | 85.0 |
| 13 | 15 | | 2.0 | Tetrafluoroethylene | $CF_2=CF_2$ | 15.8 | 87.5 |
| 14 | 20 | 3.7 | 3.0 | 1-Hydropentafluoroethane | $CF_3CF_2H$ | 36.6 | 92.5 |
| 15 | 20.0 | — | 1.0 | Trifluoroethylene | $CF_2=CFH$ | 9.8 | 88.3 |
| 16 | 15.0 | 2.0 | 2.0 | Perfluoromethylvinyl ether | $CF_3OCF=CF_2$ | 20.4 | 93.2 |
| 17 | 16 | 3.0 | 2.0 | 1-Hydropentafluoroethane | $CF_3CF_2H$ | 21.2 | 98.1 |
| 18 | 30 | 5.1 | 2.0 | 2-Hydroheptafluoropropane | $CF_3CFHCF_3$ | 41.2 | 92.0 |
| 19 | 25 | 3.5 | 2.0 | 2-Hydroperfluorobutane | $CF_3CF_2CFHCF_3$ | 45.1 | 93.5 |

What is claimed is:

1. A process for producing fluorinated aliphatic compounds comprising the following steps:
   a) providing a catalyst comprising a carrier that is promotable with alkali metal halides and at least one alkali metal halide that promotes the carrier;
   b) introducing the catalyst into a reactor and creating a reaction zone in the reactor having a temperature in the range of about 100° C. to about 450° C.;
   c) introducing into the reaction zone a starting reagent selected from the group consisting of perfluorocarboxylic acids, polyfluorocarboxylic acids and derivatives thereof, said starting reagent consisting essentially of carbon, hydrogen, oxygen and fluorine and, optionally, another halogen, whereby to cause the starting reagent to contact the catalyst in the reaction zone and to undergo pyrolysis to obtain an unsaturated aliphatic compound selected from the group consisting of perfluoroolefins, polyfluoroolefins and derivatives thereof.

2. The process according to claim 1, wherein the carrier consists of compounds selected from the group consisting of active carbon, silicon oxides, oxides of metals of Group II, III or IV of the Periodic Table, and transition metal oxides.

3. The process according to claim 2, wherein the carrier comprises a metal oxide selected from the group consisting of magnesium oxide, calcium oxide, barium oxide, zinc oxide, aluminum oxide, and nickel oxide.

4. The process according to claim 1, wherein the alkali metal halide is selected from the group consisting of fluorides, chlorides, bromides, and iodides of sodium, potassium, rubidium or cesium.

5. The process according to claim 1, wherein the catalyst is formed by mixing the carrier with an aqueous solution of the alkali metal halide and then drying to a constant weight.

6. The process according to claim 5, wherein the catalyst has a content of alkali metal halides within a range of about 20–50% by weight.

7. The process according to claim 1, further comprising a step (d) of recovering the unsaturated aliphatic compound.

8. The process according to claim 7, wherein the process consists essentially of said steps (a)–(d).

9. The process according to claim 8, wherein the catalyst consists of said carrier promoted with the alkali metal halides.

10. A process for producing fluorinated aliphatic compounds, comprising the following steps:
   (a) providing a catalyst comprising a carrier that is promotable with alkali metal halides and at least one alkali metal halide that promotes the carrier:
   (b) introducing the catalyst into a reactor and creating a reaction zone in the reactor having a temperature in a range of about 100° C. to about 450° C.;
   (c) introducing into the reaction zone a starting reagent selected from the group consisting of perfluorocarboxylic acids, polyfluorocarboxylic acids and derivatives thereof; said starting reagent consisting essentially of carbon, hydrogen, oxygen and fluorine and, optionally, another halogen, whereby to cause the starting reagent to contact the catalyst in the reaction zone and to undergo pyrolysis to obtain an unsaturated aliphatic compound selected from the group consisting of perfluoroolefins, polyfluoroolefins and derivatives thereof; and
   (d) introducing hydrogen fluoride into the reaction zone to cause a hydrofluorination of the unsaturated aliphatic compound with formation of a fluorinated aliphatic compound selected from the group consisting of polyfluoroalkanes and derivatives thereof.

11. The process according to claim 10, wherein the hydrogen fluoride is introduced into the reaction zone simultaneously with the starting reagent.

12. The process according to claim 10, wherein the hydrogen fluoride is introduced into the reaction after the pyrolysis in step (c).

13. The process according to claim 10, wherein the carrier of compounds selected from the group consisting of active carbon, silicon oxides, of metals of Group II, III or IV of the Periodic Table, and transition metal oxides.

14. The process according to claim 13, wherein the carrier comprises a metal oxide selected from the group consisting of magnesium oxide, calcium oxide, barium oxide, zinc oxide, aluminum oxide, and nickel oxide.

15. The process according to claim 10, wherein the catalyst is formed by mixing the carrier with an aqueous solution of the alkali metal halide and then drying to a constant weight.

16. The process according to claim 15, wherein the catalyst has a content of the alkali metal halides within a range of about 20–50% by weight.

17. The process according to claim 10, wherein the hydrogen fluoride is introduced into the reaction zone in an amount of 1.5–2 moles per mole of the starting reagent.

18. The process according to claim 10 comprising a step (e) of recovering the fluorinated aliphatic compound.

19. The process according to claim 18, wherein the process consists essentially of said steps (a)–(e).

20. The process according to claim 19, wherein the catalyst consists of said carrier promoted with the alkali metal halides.

21. The process according to claim 1, wherein the reactor is charged with components consisting essentially of the catalyst and the starting reagent during said process.

22. The process according to claim 21, wherein the starting reagent consists of carbon, hydrogen, oxygen, fluorine and, optionally, another halogen.

23. The process according to claim 10, wherein the reactor is charged with components consisting essentially of the catalyst and the starting reagent during said process.

24. The process according to claim 23, wherein the starting reagent consists of carbon, hydrogen, oxygen, fluorine and, optionally, another halogen.

* * * * *

UNITED STATES PATENT AND TRADEMARK OFFICE
CERTIFICATE OF CORRECTION

PATENT NO. : 6,664,431 B2
DATED : December 16, 2003
INVENTOR(S) : Sergei Mikhailovich Igumnov et al.

It is certified that error appears in the above-identified patent and that said Letters Patent is hereby corrected as shown below:

Column 10,
Line 56, after "carrier" insert -- consists -- and
Line 58, after "oxides ," insert -- oxides --.

Signed and Sealed this

Eighteenth Day of May, 2004

JON W. DUDAS
*Acting Director of the United States Patent and Trademark Office*